US00PP25965P2

(12) United States Plant Patent
Braam

(10) Patent No.: US PP25,965 P2
(45) Date of Patent: Sep. 29, 2015

(54) ***NEPHROLEPIS* PLANT NAMED 'BRAVIT2626'**

(50) Latin Name: *Nephrolepis exaltata*
Varietal Denomination: BRAVIT2626

(71) Applicant: Wim Braam, Kudelstaart (NL)

(72) Inventor: Wim Braam, Kudelstaart (NL)

(73) Assignee: Braam Vitro B.V., De Kwakel (NL)

( * ) Notice: Subject to any disclaimer, the term of this patent is extended or adjusted under 35 U.S.C. 154(b) by 98 days.

(21) Appl. No.: 13/998,709

(22) Filed: Nov. 26, 2013

(51) Int. Cl.
*A01H 5/00* (2006.01)

(52) U.S. Cl.
USPC ..... Plt./379

(58) Field of Classification Search
USPC ..... Plt./379
See application file for complete search history.

*Primary Examiner* — Susan McCormick Ewoldt
(74) *Attorney, Agent, or Firm* — C. A. Whealy

(57) ABSTRACT

A new and distinct cultivar of *Nephrolepis* plant named 'BRAVIT2626' characterized by its upright to outwardly arching plant habit; dark green-colored pinnae; and good postproduction performance.

2 Drawing Sheets

Botanical designation: *Nephrolepis exaltata.*
Cultivar denomination: 'BRAVIT2626'.

BACKGROUND OF THE INVENTION

The present invention relates to a new and distinct cultivar of *Nephrolepis* plant, botanically known as *Nephrolepis exaltata*, commonly known as Sword Fern and hereinafter referred to by the name 'BRAVIT2626'.

The new *Nephrolepis* plant is a naturally-occurring whole plant mutation of *Nephrolepis exaltata* 'Green Lady', not patented. The new *Nephrolepis* plant was discovered and selected by the Inventor as a single plant within a population of plants of 'Green Lady' in a controlled greenhouse environment in De Kwakel, The Netherlands in March, 2012.

Asexual reproduction of the new *Nephrolepis* plant by tissue culture in De Kwakel, The Netherlands, since May, 2012 has shown that the unique features of this new *Nephrolepis* plant are stable and reproduced true to type in successive generations.

SUMMARY OF THE INVENTION

Plants of the new *Nephrolepis* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BRAVIT2626'. These characteristics in combination distinguish 'BRAVIT2626' as a new and distinct *Nephrolepis* plant:

1. Upright to outwardly arching plant habit.
2. Dark green-colored pinnae.
3. Good postproduction performance.

Plants of the new *Nephrolepis* differ from plants of the mutation parent, 'Green Lady', in the following characteristics:

1. Plants of the new *Nephrolepis* are more outwardly arching than and not as upright as plants of 'Green Lady'.

2. Plants of the new *Nephrolepis* grow faster than plants of 'Green Lady'.
3. Plants of the new *Nephrolepis* have longer fronds than plants of 'Green Lady'.
4. Plants of the new *Nephrolepis* have slightly lighter green-colored pinnae than plants of 'Green Lady'.

Plants of the new *Nephrolepis* can be compared to plants of *Nephrolepis exaltata* 'True Boston', not patented. Plants of the new *Nephrolepis* differ primarily from plants of 'True Boston' in the following characteristics:

1. Plants of the new *Nephrolepis* are more compact than plants of 'True Boston'.
2. Plants of the new *Nephrolepis* have shorter fronds than plants of 'True Boston'.
3. Plants of the new *Nephrolepis* have darker green-colored pinnae than plants of 'True Boston'.
4. Pinnae of plants of the new *Nephrolepis* maintain their dark green color with development whereas pinnae of plants of 'True Boston' become chlorotic with development.

BRIEF DESCRIPTION OF THE PHOTOGRAPHS

The accompanying colored photographs illustrate the overall appearance of the new *Nephrolepis* plant showing the colors as true as it is reasonably possible to obtain in colored reproductions of this type. Colors in the photographs may differ slightly from the color values cited in the detailed botanical description which accurately describe the colors of the new *Nephrolepis* plant.

The photograph on the first sheet is a side perspective view of a typical flowering plant of 'BRAVIT2626' grown in a container.

The photograph on the second sheet is a close-up view of the upper and lower surfaces of typical fronds of 'BRAVIT2626'.

DETAILED BOTANICAL DESCRIPTION

Plants used for the aforementioned photographs and following description were grown during the summer in twoliter containers in a glass-covered greenhouse in De Kwakel, The Netherlands and under cultural practices typical of commercial production conditions. During the production of the plants, day and night temperatures ranged from 18.5° C. to 22.5° C. and light levels averaged 20,000 lux. Plants were one year old when the photographs and description were taken. In the following description, color references are made to The Royal Horticultural Society Colour Chart, 2007 Edition, except where general terms of ordinary dictionary significance are used.

Botanical classification: *Nephrolepis exaltata* 'BRAVIT2626'.

Parentage: Naturally-occurring whole plant mutation of *Nephrolepis exaltata* 'Green Lady', not patented.

Propagation:

*Type*.—By tissue culture.

*Time to initiate roots, summer*.—About ten days at temperatures about 21° C.

*Time to initiate roots, winter*.—About two weeks at temperatures about 21° C.

*Time to produce a rooted young plant, summer*.—About three weeks at temperatures about 21° C.

*Time to produce a rooted young plant, winter*.—About four weeks at temperatures about 21° C.

*Root description*.—Fine, fibrous; white in color.

*Rooting habit*.—Freely branching; dense.

Plant description:

*Plant and growth habit*.—Upright to outwardly arching plant habit; moderately vigorous to vigorous growth habit; suitable for interiorscape usage.

*Plant height*.—About 98 cm.

*Plant width*.—About 74 cm.

Frond description:

*Frond length*.—About 44.7 cm.

*Frond width*.—About 9 cm.

*Frond shape*.—Narrowly lanceolate.

*Rachis length*.—About 44.4 cm.

*Rachis width*.—About 1.5 mm

*Rachis strength*.—Strong, moderately flexible.

*Rachis texture*.—Densely pubescent.

*Rachis/frond orientation*.—Mostly straight.

*Rachis color*.—Close to 152C; pubescence, close to 164B to 164C.

Pinnae description:

*Arrangement*.—Bi-pinnate.

*Quantity per frond*.—About 76.

*Length*.—About 4.4 cm.

*Width*.—About 1.1 cm.

*Shape*.—Narrowly lanceolate; moderately carinate.

*Apex*.—Obtuse to bluntly acute.

*Base*.—Truncate to obtuse.

*Margin*.—Entire; slightly undulate.

*Texture, upper and lower surfaces*.—Smooth, glabrous.

*Venation pattern*.—Pinnate.

*Color*.—Developing pinnae, upper surface: Close to 145A; towards the base, close to 144A to 144B. Developing pinnae, lower surface: Close to 145A; towards the base, close to 144B. Fully developed pinnae, upper surface: Between 137B and 146A; venation, close to 147A. Fully developed pinnae, lower surface: Close to 137C to 137D; venation, close to 203A.

*Petioles*.—Length (proximal pinnae): About 7.8 cm. Width: About 1.5 mm. Texture, upper and lower surfaces: Pubescent. Color, upper and lower surfaces: Close to 152C; proximally, close to N199B.

Spore description: Spore development has not been observed on plants of the new *Nephrolepis*.

Disease & pest resistance: Plants of the new *Nephrolepis* have not been observed to be resistant to pathogens and pests common to *Nephrolepis* plants.

Interiorscape performance: Plants of the new *Nephrolepis* have exhibited good interiorscape performance.

Temperature tolerance: Plants of the new *Nephrolepis* have been observed to tolerate high temperatures about 35° C. and to be hardy to USDA Hardiness Zone 10.

It is claimed:

1. A new and distinct *Nephrolepis* plant named 'BRAVIT2626' as illustrated and described.

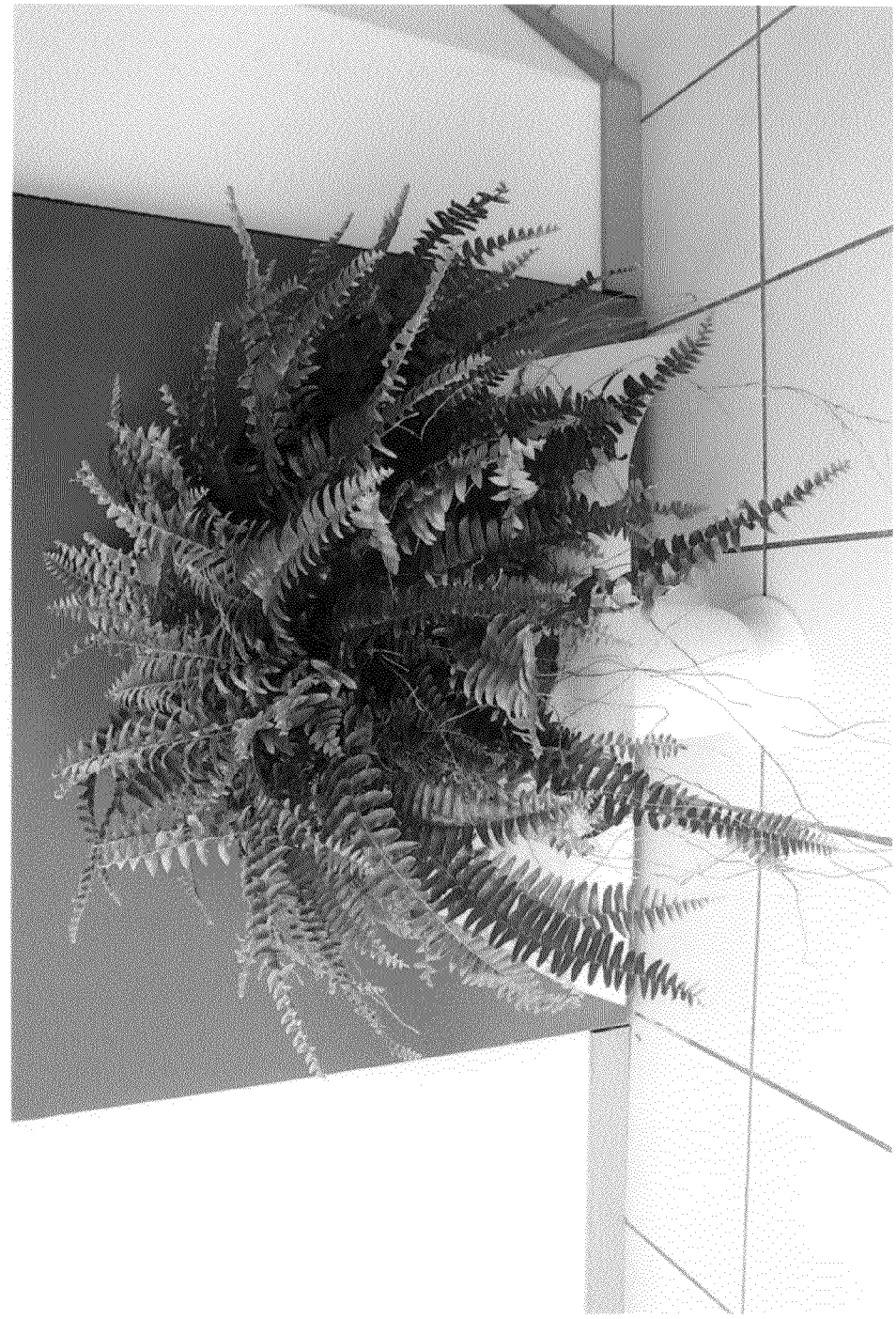

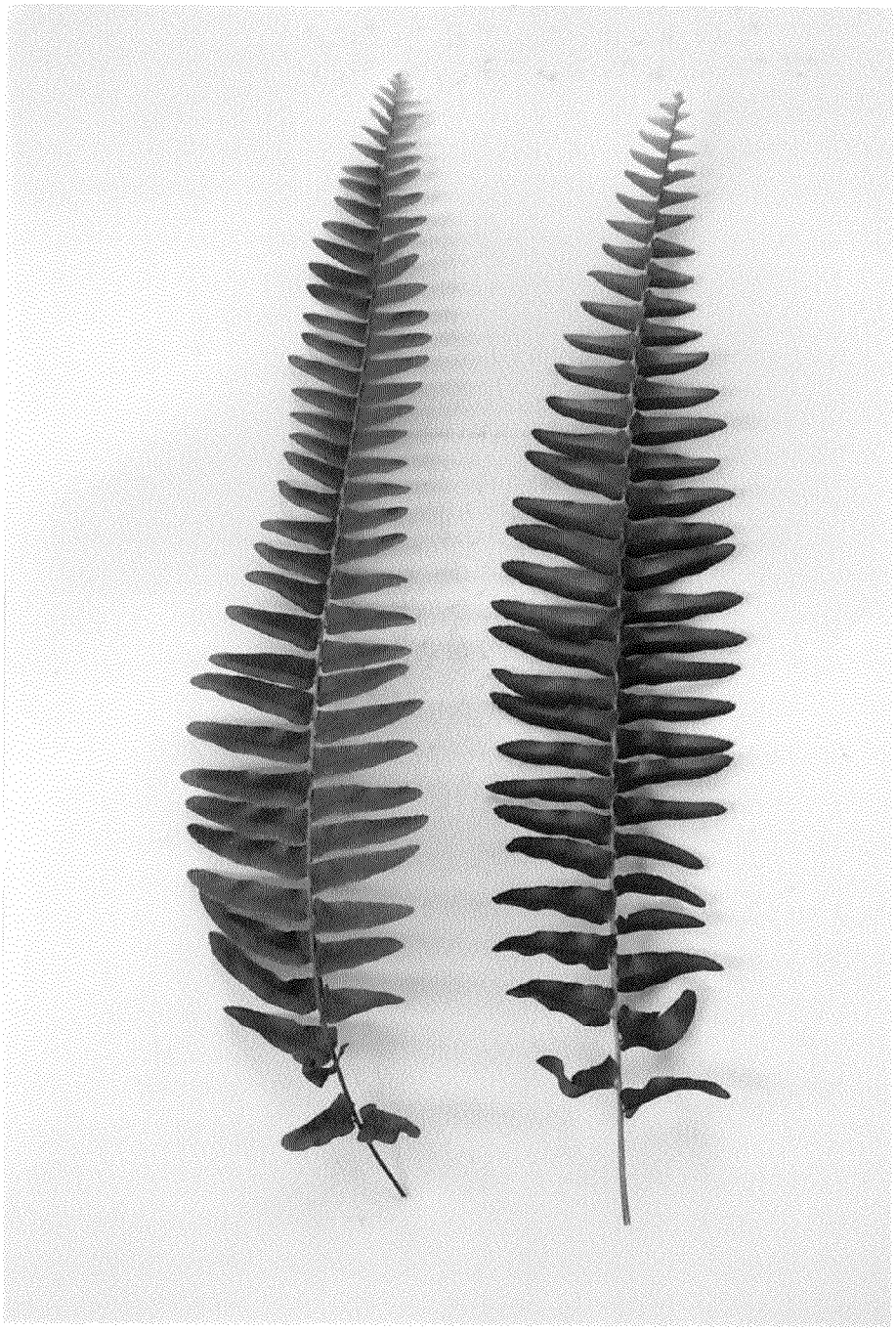

* * * * *